United States Patent [19]

Schlereth et al.

[11] 4,164,861

[45] Aug. 21, 1979

[54] LEAK STANDARD GENERATOR

[75] Inventors: Fritz H. Schlereth, Baldwinsville; Michael J. Morgan, Syracuse, both of N.Y.

[73] Assignee: Inficon Leybold-Heraeus Inc., East Syracuse, N.Y.

[21] Appl. No.: 878,768

[22] Filed: Feb. 17, 1978

[51] Int. Cl.² .............................................. B01B 17/00

[52] U.S. Cl. ...................................................... 73/1 G

[58] Field of Search ................ 73/1 G; 122/4 R, 4 A; 261/139

[56] References Cited

U.S. PATENT DOCUMENTS

| | | | |
|---|---|---|---|
| 2,981,091 | 4/1961 | Roberts | 73/1 G |
| 3,516,278 | 6/1970 | Klein et al. | 73/1 G |
| 4,036,915 | 7/1977 | Lucero | 73/1 G |

*Primary Examiner*—S. Clement Swisher
*Attorney, Agent, or Firm*—Bruns & Jenney

[57] ABSTRACT

A leak standard generator which utilizes the diffusion properties of a gas or vapor to deliver a uniform rate of flow of a leak sample into a diluent gas stream. The generator includes a reservoir containing the leak sample, a discharge head through which is passed a metered flow of diluent gas and a diffusion tube of prescribed dimensions for carrying a gas or vapor of the sample from the reservoir into the diluent gas stream moving through the discharge head. Heating means are provided to maintain the reservoir and the diffusion tube at different temperature levels to promote uniform movement of the sample gas or vapor into the diluent stream.

16 Claims, 3 Drawing Figures

11
10
13
14
12
35
39
38
12
36
40

46
62
63
60
R1
R2
R3
33
10 VDC
45
62
63
61
R1
R2
R4
R5
47

LEAK STANDARD GENERATOR

BACKGROUND OF THE INVENTION

This invention relates to a leak standard generator suitable for calibrating highly sensitive quantitative detectors. More specifically, this invention relates to a relatively simple leak generator capable of delivering accurate standards at extremely low leak rates.

Many leak standard generators in use today rely upon capillary action for supplying a metered leak standard. As disclosed by Christensen in U.S. Pat. No. 3,760,773, the sample material is typically stored in a housing in liquid form and the material heated to produce a vapor thereof. The high temperature vapor, which is at a correspondingly high pressure, is expanded rapidly through a capillary tube or orifice into a region of lower pressure. By accurately controlling the conditions on both the high and low pressure sides of the capillary device within prescribed parameters, a predictable rate of flow of the sample material through the capillary can be maintained. The equipment needed to control the pressure differential over the capillary, however, is generally costly and difficult to maintain within the generally narrow operating limits. Similarly, the turbulence, which is generally associated with the capillary flashing action, can make it somewhat difficult to achieve accurate flow metering at the low leak rates needed to calibrate truly sensitive detectors. Furthermore, the heated vapor generated in the housing tends to condense on the generally cooler walls of the capillary device. This condensation can have a deleterious effect on the operation of the generator at these low flow rates.

The present leak generator relies upon the diffusion properties exhibited by all gases and vapors to provide for a simple but extremely accurate generator capable of delivering leak standards of a sample material at extremely low leak rates.

SUMMARY OF THE INVENTION

It is therefore an object of the present invention to improve leak standard generators.

A further object of the present invention is to provide a leak standard generator that can be accurately and simply controlled to supply a desired flow rate of a sample material into a diluent gas.

A still further object of the present invention is to utilize the diffusion properties of a gas or a vapor to provide a leak standard generator capable of delivering a predictable and uniform output at extremely low flow rates.

These and other objects of the present invention are attained by means of a leak generator including a sealed reservoir containing a leak sample, a discharge head through which is passed a metered amount of a diluent gas, an enclosed conduit of predetermined dimensions being arranged to diffuse a gas or vapor of the leak sample generated in the reservoir into a diluent gas passing through the discharge head, a first heating means to maintain the reservoir at a temperature level wherein the sample is at least partially vaporized, a second heating means to maintain the conduit at a temperature level sufficient to prevent the diffusion sample passing therethrough from condensing, and control means for regulating the operation of said first and second heating means.

BRIEF DESCRIPTION OF THE DRAWINGS

For a better understanding of the present invention as well as other objects and further features thereof, reference is had to the following detailed description of the invention to be read in conjunction with the accompanying drawings wherein.

DESCRIPTION OF THE PREFERRED EMBODIMENT

Figure 1:
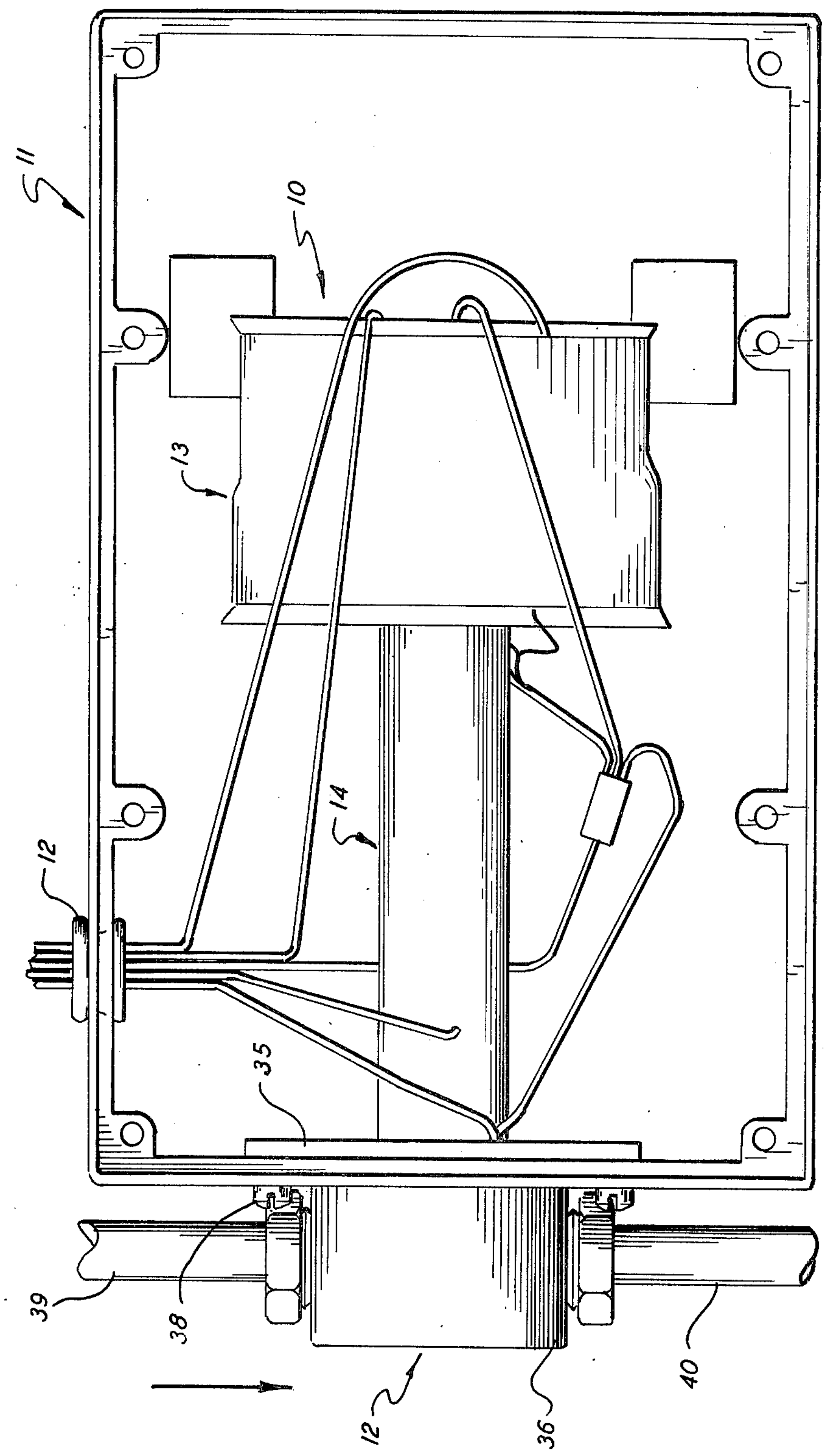
FIG. 1 is a plan view of the leak generator of the present invention showing the generator contained within a protective housing.

A leak standard generator 10, embodying the teachings of the present invention, is shown in FIG. 1 contained within a protective housing 11. Although removed for the sake of clarity, the housing is furnished with a bolt-on cover which is, in assembly, secured to the sidewalls of the housing to substantially enclose the generator therein. As will be described in further detail below, the generator includes a plurality of heaters which carry out important functions in relation to the operation of the device. With the cover in place, the housing serves as an air oven in the system for holding the energy developed by the heaters about the surface of the generator thus improving the overall thermal efficiency of the system. The housing further serves to protect the normally exposed sensitive electrical components from being damaged. The wiring to the various electrical components is brought out of the housing at a single location through a grommet 12 that is supported in one of the housing sidewalls and which functions to preserve the thermal integrity of the oven.

The generator is formed of three main sections that include a sealed sample reservoir 13, a diffusion tube oven 14 containing a diffusion tube 16, and a metering head 15. In assembly, the diffusion tube is spirally wound within the oven 14 and is arranged to carry a leak sample from the reservoir to the metering head by means of a simple diffusion process. The tube oven is made of a cylindrical member 17, preferably formed of stainless steel, that is closed at both ends by end bushings 18 and 19. Each end bushing is supplied with an axial opening passing therethrough adapted to receive in close sliding relationship therewith the two axially extended terminal ends of the diffusion tube. Both the feed end 26 and the discharge end 27 of the diffusion tube are cemented in place and sealed in assembly using any suitable epoxy resin 22 applied to the tube-to-bushing joint. The end bushings are similarly cemented to the cylinder, using the same type of resin, to provide for a sealed unit.

Figure 2:
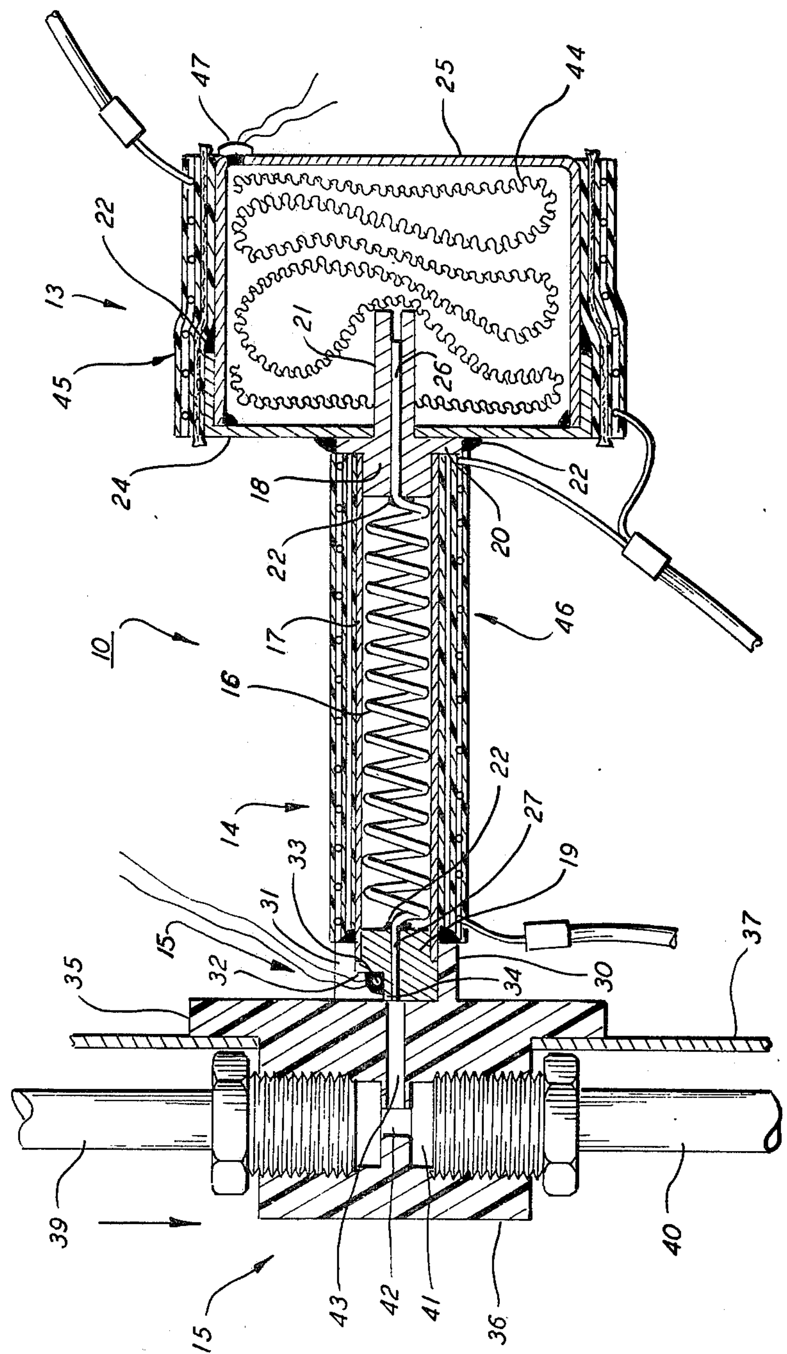
FIG. 2 is a sectional view taken along the axial centerline of the generator shown in FIG. 1 illustrating in detail the various generator components.

As best illustrated in FIG. 2, the lower end bushing 18 contains a radially extended flange 20 and an axially extended section 21 depending outwardly from the flange. In assembly, the extended section is inserted into the reservoir through an opening provided in its top cover 24 thereof and the flange is securely seated in contact against the top surface of the cover. As in the case of the diffusion tube oven, the flange is cemented to the reservoir cover and the cover in turn cemented to reservoir body 25 to provide for a sealed reservoir unit.

The opposite end bushing 19 is slidably received within a dependent hub 30, which is carried on the bottom of the metering head 15, and is sealed in place again using epoxy resin. Hub 30 contains an axially extended opening 31 in its sidewall which, in assembly, allows access to an undercut section 32 formed in the underlying portion of the end bushing. The undercut is brought to a radial depth so that only a relatively thin wall 34 separates the discharge end 27 of the diffusion tube and the bottom surface of the undercut. A thermal sensor, preferably in the form of a glass bead thermistor 33, is located at the bottom of the undercut in close proximity with the discharge end of the tube. Wall 34 is thin enough so that the sensor can quickly detect any change in the thermal condition of the diffusion tube within its critical discharge region. The sensor leads are brought out of the assembly via the opening 31 formed in the hub and are electrically connected into a control circuit, the function of which will be explained in further detail below.

Metering head 15 is preferably fabricated from a single piece of plastic material and, in addition to the previously noted hub, includes a mounting flange 35 and a cylindrical body member 36 depending outwardly therefrom. In practice, the mounting flange is located within housing 11 and is positioned in abutting contact against sidewall 37 thereof with the body member 36 of the head extending outwardly through an opening provided in the sidewall. The flange is secured to the housing by means of mounting screws 38 as shown in FIG. 1.

In operation, a continuous flow of diluent gas is passed through the body section of the metering head which is located outside of the housing 11. The diluent gas is carried into the head via inlet line 39 and away from the head by means of discharge line 40. A restriction 42 is contained within the diluent gas flow passage 41 formed in the metering head which serves to regulate the amount of diluent gas moving therethrough. An axially aligned passage 43 is also formed in the metering head for placing the restriction region 42 in fluid flow communication with the discharge end of the diffusion tube to permit diffusing vapors of a sample material stored in the reservoir to be metered into the diluent gas stream.

Sample reservoir 13 is wrapped with a heater blanket 45 designed to hold the temperature of the reservoir at a desired operating level. In practice, any suitable device capable of holding the reservoir at a constant prescribed temperature may be utilized in the present invention. As shown, the blanket typically consists of a nichrome wire element enclosed within an electrical insulating material that is adapted to distribute the heat generated in the wire evenly about the surface of the reservoir. By controlling the amount of current supplied to the blanket, it is possible to maintain the reservoir at a desired temperature level.

In practice, the sample material, which is typically a liquid, is placed in the reservoir and the reservoir sealed as described using an epoxy resin or the like. A wick 44, made of lint free optical cloth, is located within the reservoir. The wick absorbs the sample material and evenly distributes it throughout the interior of the housing. This provides for more efficient evaporation of the sample, avoids hot spots from developing within the reservoir and prevents splash evaporation from occurring.

A second heater blanket 46, similar to that associated with the sample reservoir, is wrapped about the exterior of the cylindrical tube oven. As will be explained in greater detail below, an independent circuit means is provided to the oven heater for holding the oven, and thus the tube spirally wound therein, at a separate lower temperature than that maintained within the reservoir.

In the present generator, the diluent gas moved through the metering head is permitted to move down the diffusion tube and into the sealed reservoir to establish a controlled atmosphere therein. The temperature of the reservoir is then raised to bring the sample to a temperature somewhere between its saturation and boiling temperatures whereby the liquid is partially vaporized to create a known partial pressure within the reservoir.

As is well known, molecules of a vapor, under these conditions, will distribute themselves uniformly in the confined atmosphere and are perfectly miscible in the atmosphere gas. As a result, the partially vaporized sample will diffuse up the tube at a controlled and predictable rate to supply an accurate leak standard at the metering head. The leak rate can be determined by the following relationship:

$$qd = \frac{DMPA}{LRT} (\text{Log})n \frac{P}{(P - pv)}$$

where qd is the flow rate of a diffusing sample through the conduit;

D is the diffusion coefficient of the sample gas or vapor;

M is the molecular weight of the sample gas or vapor;

P is the atmospheric pressure;

Pv is the partial vapor pressure of the sample within the generator;

R is the molar gas constant of the sample gas or vapor;

T is the temperature absolute of the generator;

L is the length of the diffuser conduit;

A is the area of the diffusion conduit; and (Log)n is the natural log of the function.

As can be seen, by constructing a generator in the manner herein described, the diffusion rate through the tube is solely dependent upon the partial vapor pressure generated within the reservoir. This, in turn, is simply controlled by controlling the operating temperature of the reservoir.

It has been found that the vapors generated in the reservoir tend to condense on the walls of the diffusion tube, particularly in the bend regions, as the sample vapor diffuses through the diluent gas. To overcome this difficulty, the temperature of the diffusion tube is brought to an operating level slightly above the condensation temperature of the vapor by means of the oven heater blanket. As noted, the critical condensation region is found at the discharge end of the tube at the point where the sample is leaked into the flow of diluent gas. Sensor 33 (FIG. 2), which acts in conjunction with the oven heater control circuit, is mounted in this region to detect thermal conditions at the discharge end of the tube and, as will be explained below, institutes suitable action to insure that the diffusing vapor moves in an unimpeded manner into the diluent gas stream.

Figure 3:
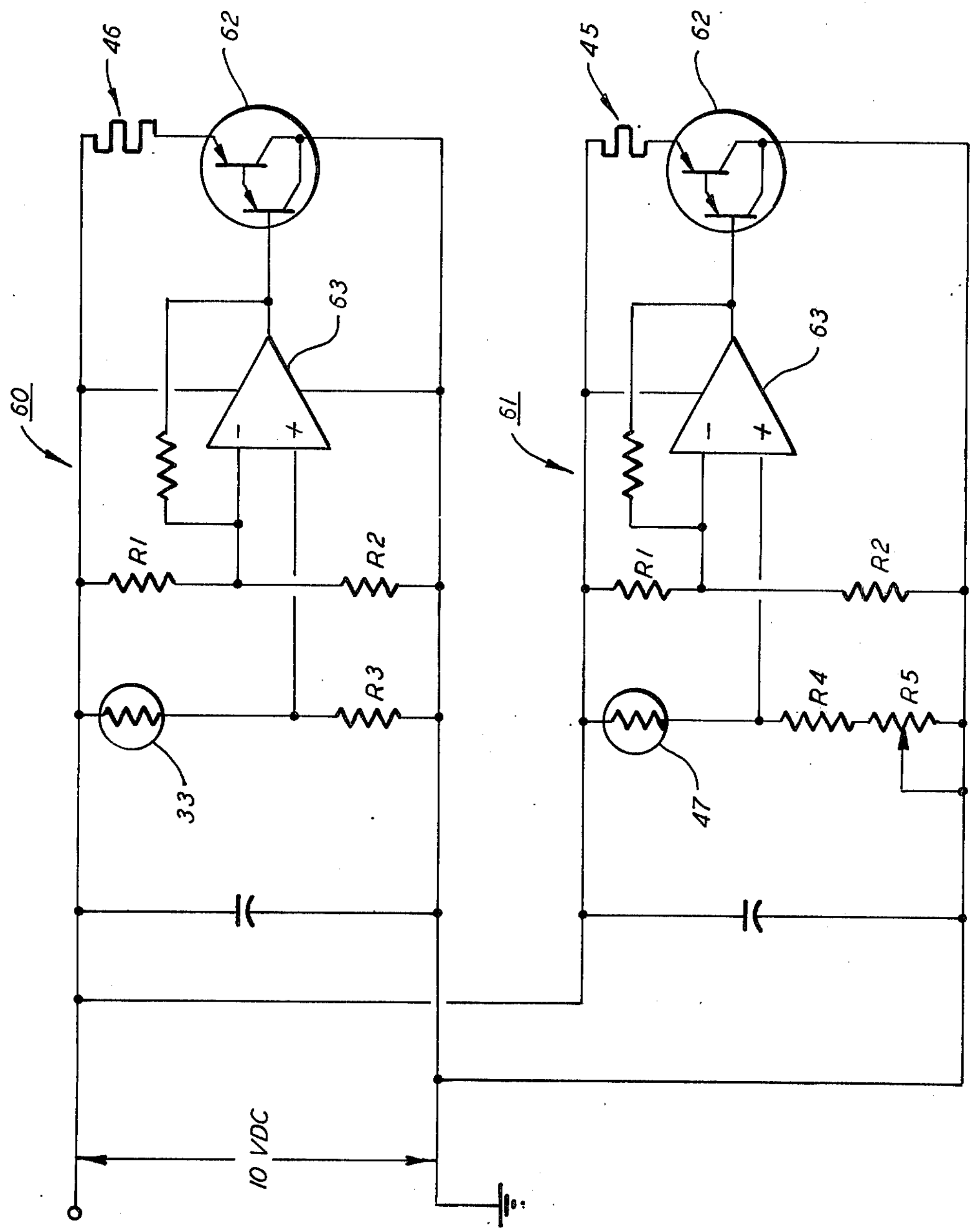
FIG. 3 is an electrical diagram including control circuits for regulating the operation of heaters utilized in the instant generator.

Referring now to FIG. 3, there is illustrated a schematic diagram of an electrical control system for maintaining the cylindrical diffusion tube oven and the sample reservoir at separate temperatures. In this embodiment of the invention, the reservoir is maintained at a temperature at which the liquid sample contained therein is partially vaporized. The tube oven temperature on the other hand is brought to a lower temperature at which the vapors diffusing through the tube are prevented from condensing on the wall of the tube. The electrical system is made up of two similar control circuits that include the diffusion tube oven control circuit 60 and the sample reservoir control circuit 61. Each circuit is made up of solid state components which operate in a similar manner to provide a highly reliable control network.

The tube oven heater 46, which consists of a Nichrome wire spirally wound about the outer surface of the oven, is shown schematically in control circuit 60. Heater 45, surrounding the reservoir, is also schematically represented in control circuit 61. A 10 volt DC power supply is arranged to provide power to both circuits. Each heater is powered by a PNP Darlington amplifier 62 that is electrically adapted to operate as an emitter follower in the respective circuits and thus remain conductive over the operating range of the system. The transistors, in turn, are both driven by an operational amplifier 63 that is employed in the circuit as a voltage comparitor.

The negative, or inverted input to each comparator is held at a prescribed reference voltage by a voltage divider network made up of resistors R1 and R2. The positive, or non-inverted, voltage supplied to each comparator is provided by a second control network. In the case of the oven control circuit 60, the positive control voltage is furnished via thermistor 33, located at the critical discharge region of the diffusion tube, and a fixed resistor R3. In operation, the thermistor senses the temperature within the critical region and provides information to the comparitor for maintaining the oven at a prescribed level sufficiently high enough to thus prevent diffusing vapor from condensing as it moves into the diluent gas stream. In operation, when the temperature at the discharge end of the diffusion tube decreases, the resistance of the thermistor 33 increases proportionally. This, in turn, increases the positive voltage input to the comparator thus producing an output signal that calls for an increase in heater current. The generated output signal is applied to the amplifier thereby varying its output to regulate the amount of current supply to the heater coil 46.

The positive input to the comparator located in the reservoir control circuit 61 is furnished by a second thermistor 47, which is located physically in thermal contact with the bottom wall of the reservoir as shown in FIG. 2, acting in conjunction with a pair of resistors that include fixed resistor R4 and variable resistor R5. By adjusting the setting of the variable resistor R5, the output of the amplifier can be regulated so as to maintain the heater 45 at a desired operational temperature range.

As previously noted, the present leak generator is well suited for use in calibrating a halogen sensor for monitoring atmospheric conditions in an operating room or the like. In this embodiment, clean filtered air is used as a diluent gas into which the leak sample is diffused. The sample bearing gas is then carried to the sensor via line 40. Methoxyflurane, which is one of many anesthetics, is ideally well suited for use as a sample material in this environment. This organic material is a liquid at normal ambient conditions and possesses a vapor pressure response similar to water which permits the generator to be operated at temperatures well above ambient to provide a relatively low leak rate required to accurately calibrate a highly sensitive detector.

Although methoxyflurane is herein employed as a sample material, it should be clear to one skilled in the art that any sample material capable of being vaporized at above ambient conditions, and which exhibits suitable vaporization characteristics, can be similarly employed in the generator of the present invention without departing from the teaching of the invention. While the invention has been described with reference to the structure disclosed herein, it is not confined to the details set forth, and this application is intended to cover such modifications or changes as may come within the scope of the following claims.

We claim:

1. A leak standard generator including a discharge head for passing a metered flow of diluent gas therethrough, a sealed reservoir containing a leak sample, a diffusion tube extending between the reservoir and the discharge head, said tube being of a predetermined length and a uniform cross sectional area such that the diluent gas being metered through the discharge head is allowed to pass freely into the tube to at least partially fill said tube, and heater means operatively associated with the reservoir for maintaining the reservoir at a desired temperature level to at least partially vaporize said leak sample whereby the vapor of the sample generated in the reservoir diffuses through the diluent gas contained in said tube at a controlled rate and is discharged into the flow of diluent gas passing through said discharge head.

2. The leak standard generator of claim 1 further including a second heater means operatively associated with the diffusion tube for maintaining the temperature of the tube at a level slightly above the condensation temperature of the sample material.

3. The leak standard generator of claim 1 wherein the sample is contained in said sealed reservoir in liquid form and further including a lint free wick positioned in said reservoir adapted to absorb said liquid sample and distribute the sample uniformly throughout the reservoir.

4. The leak standard generator of claim 2 further including a sensor mounted adjacent to the discharge end of the diffusion tube for sensing the temperature therein and control means for regulating the temperature of said second heater in response to said sensor.

5. The leak standard generator of claim 4 wherein said second heater means includes an oven extending between said reservoir and said discharge head that is arranged to substantially enclose said tube, and a heater blanket wrapped about said oven.

6. A leak standard generator suitable for use in calibrating a halogen sensor for monitoring an atmosphere including a sealed reservoir containing a material for generating a leak sample, a discharge head for passing a metered flow of a diluent gas to a sensor, a diffusion conduit extending between the reservoir and the discharge head that is of a uniform cross sectional area such that the diluent gas passing through the discharge head is allowed to at least partially fill said conduit, a first heater blanket surrounding the reservoir for maintaining the reservoir at a uniform temperature to at least partially vaporize said sample and cause the sample to diffuse through the diluent gas contained in the conduit and be passed into the flow of said gas metered through said head, a second heater blanket surrounding the diffusion conduit for maintaining the conduit at a second temperature level slightly above the condensing temperature of said sample material, and control means operatively associated with said first and second heater blankets for independently holding each heater blanket at a separate temperature level.

7. The generator of claim 6 wherein said control means further includes means to vary the temperature of said reservoir.

8. The generator of claim 6 wherein said sample is methoxyflurane and said diluent gas is clean filtered air.

9. The generator of claim 8 wherein said methoxyflurane is contained in liquid form within said reservoir and further including a wick, positioned within the reservoir, for absorbing said sample.

10. The generator of claim 6 further including a temperature sensor arranged to secure the temperature at the discharge end of said diffusion conduit and to regulate the temperature of said second heater blanket in response therewith.

11. The generator of claim 6 further including a thermal tight housing substantially enclosing the reservoir and the diffusion conduit.

12. A method of generating a leak standard of a sample material suitable for use in calibrating a detector or the like including the steps of partially vaporizing a leak sample within a substantially enclosed cell of given volume to create a partial pressure of said vapor within the cell, diffusing the vapor of said sample generated within the cell through a conduit of prescribed dimensions which contains a diluent gas whereby the diffusing vapor is passed into the diluent gas at an accurately controlled rate, and discharging the diffused vapor into a metered flow of said diluent gas.

13. The method of claim 12 wherein partial vaporization of the sample is accomplished by heating the cell to a predetermined temperature.

14. The method of claim 13 further including the step of maintaining the diffusion conduit at a temperature such that the diffusing vapors passing therethrough are prevented from condensing within the conduit.

15. The method of claim 14 further including the steps of sensing the temperature of said conduit at the discharge end thereof, and controlling the temperature of said conduit in response to the temperature sensed.

16. The method of claim 12 further including the step of absorbing the sample material in liquid form into a wick contained within the cell.

* * * * *